(12) United States Patent
Kroll et al.

(10) Patent No.: US 7,706,864 B2
(45) Date of Patent: *Apr. 27, 2010

(54) METHOD AND APPARATUS FOR ELECTRICALLY FORCING CARDIAC OUTPUT IN AN ARRHYTHMIA PATIENT

(75) Inventors: Kai Kroll, Minneapolis, MN (US); Mark W. Kroll, Simi Valley, CA (US)

(73) Assignee: Galvani, Ltd., Minneapolis, MN (US)

( * ) Notice: Subject to any disclaimer, the term of this patent is extended or adjusted under 35 U.S.C. 154(b) by 1612 days.

This patent is subject to a terminal disclaimer.

(21) Appl. No.: 10/429,509

(22) Filed: May 5, 2003

(65) Prior Publication Data
US 2004/0044373 A1 Mar. 4, 2004

Related U.S. Application Data

(63) Continuation of application No. 09/693,455, filed on Oct. 20, 2000, now Pat. No. 6,560,484, which is a continuation of application No. 09/277,311, filed on Mar. 26, 1999, now Pat. No. 6,185,457, which is a continuation-in-part of application No. 08/754,712, filed on Dec. 6, 1996, now Pat. No. 5,978,703, which is a continuation of application No. 08/543,001, filed on Oct. 13, 1995, now abandoned, which is a continuation of application No. 08/251,349, filed on May 31, 1994, now abandoned.

(51) Int. Cl.
*A61B 5/04* (2006.01)
(52) U.S. Cl. .................................................. 600/509
(58) Field of Classification Search ............... 607/4–9, 607/28; 600/508, 509
See application file for complete search history.

(56) References Cited

U.S. PATENT DOCUMENTS

| 3,638,656 A | 2/1972 | Grandjean et al. |
|---|---|---|
| 3,703,900 A | 11/1972 | Holznagel |
| 3,923,060 A | 12/1975 | Ellinwood Jr. |
| 3,952,750 A | 4/1976 | Mirowski et al. |
| 4,003,379 A | 1/1977 | Ellinwood, Jr. |
| 4,146,029 A | 3/1979 | Ellinwood, Jr. |

(Continued)

FOREIGN PATENT DOCUMENTS

EP 0 540 266 A1 10/1993

(Continued)

OTHER PUBLICATIONS 5,584,866, Dec. 1996, Kroll et al. (withdrawn).

(Continued)

*Primary Examiner*—George Manuel
(74) *Attorney, Agent, or Firm*—Patterson, Thuente, Skaar & Christensen, P.A.

(57) ABSTRACT

An electrical method and apparatus for stimulating cardiac cells causing contraction to force hemodynamic output during fibrillation, hemodynamically compromising tachycardia, or asystole. Forcing fields are applied to the heart to give cardiac output on an emergency basis until the arrhythmia ceases or other intervention takes place. The device is used as a stand alone external or internal device, or as a backup to an ICD, atrial defibrillator, or an anti-tachycardia pacemaker. The method and apparatus maintain some cardiac output and not necessarily defibrillation.

72 Claims, 8 Drawing Sheets

U.S. PATENT DOCUMENTS

| | | | |
|---|---|---|---|
| 4,181,133 A | | 1/1980 | Kolenik et al. |
| 4,222,386 A | | 9/1980 | Smolmikov et al. |
| 4,280,502 A | | 7/1981 | Baker, Jr. et al. |
| 4,349,030 A | | 9/1982 | Belgard et al. |
| 4,390,021 A | | 6/1983 | Spurrell et al. |
| 4,398,536 A | | 8/1983 | Nappholz et al. |
| 4,408,606 A | | 10/1983 | Spurrell et al. |
| 4,488,553 A | | 12/1984 | Nappholz et al. |
| 4,488,554 A | | 12/1984 | Nappholz et al. |
| 4,552,561 A | | 11/1985 | Eckenhoff et al. |
| 4,559,946 A | | 12/1985 | Mower |
| 4,572,191 A | | 2/1986 | Mirowski et al. |
| 4,686,988 A | * | 8/1987 | Sholder ..................... 607/28 |
| 4,693,253 A | | 9/1987 | Adams |
| 4,774,950 A | | 10/1988 | Cohen |
| 4,830,006 A | | 5/1989 | Haluska et al. |
| 4,945,909 A | | 8/1990 | Feranot et al. |
| 4,969,873 A | | 11/1990 | Steinbach et al. |
| 4,986,270 A | | 1/1991 | Cohen |
| 4,996,984 A | | 3/1991 | Sweeney |
| 4,998,975 A | | 3/1991 | Cohen et al. |
| 5,018,522 A | | 5/1991 | Mehra |
| 5,041,107 A | | 8/1991 | Heil, Jr. |
| 5,042,497 A | | 8/1991 | Shapland |
| 5,087,243 A | | 2/1992 | Avitall |
| 5,098,442 A | | 3/1992 | Grandjean |
| 5,184,616 A | | 2/1993 | Weiss |
| 5,193,535 A | | 3/1993 | Bardy et al. |
| 5,193,537 A | | 3/1993 | Freeman |
| 5,207,219 A | | 5/1993 | Adams et al. |
| 5,220,917 A | | 6/1993 | Cammilli et al. |
| 5,222,480 A | * | 6/1993 | Couche et al. ................. 607/5 |
| 5,230,336 A | | 7/1993 | Fain et al. |
| 5,265,600 A | | 11/1993 | Adams et al. |
| 5,282,836 A | | 2/1994 | Kreyenhagen et al. |
| 5,282,837 A | | 2/1994 | Adams et al. |
| 5,305,745 A | | 4/1994 | Zacouto |
| 5,314,448 A | | 5/1994 | Kroll et al. |
| 5,330,505 A | | 7/1994 | Cohen |
| 5,330,506 A | | 7/1994 | Alferness et al. |
| 5,330,509 A | | 7/1994 | Kroll et al. |
| 5,336,245 A | | 8/1994 | Adams et al. |
| 5,350,402 A | | 9/1994 | Infinger et al. |
| 5,376,103 A | | 12/1994 | Anderson et al. |
| 5,391,185 A | | 2/1995 | Kroll |
| 5,411,524 A | | 5/1995 | Rahul |
| 5,431,688 A | | 7/1995 | Freeman |
| 5,464,434 A | | 11/1995 | Alt |
| 5,499,971 A | | 3/1996 | Shapland et al. |
| 5,527,344 A | | 6/1996 | Arzbaecher et al. |
| 5,601,611 A | | 2/1997 | Fayram et al. |
| 5,607,454 A | | 3/1997 | Cameron et al. |
| 5,662,689 A | | 9/1997 | Elsberry et al. |
| 5,700,281 A | | 12/1997 | Brewer et al. |
| 5,735,876 A | | 4/1998 | Kroll et al. |
| 5,782,883 A | | 7/1998 | Kroll et al. |
| 5,871,510 A | | 2/1999 | Kroll et al. |
| 5,913,879 A | | 6/1999 | Ferek-Petric et al. |
| 5,978,703 A | | 11/1999 | Kroll et al. |
| 6,167,306 A | | 12/2000 | Kroll et al. |
| 6,185,457 B1 | | 2/2001 | Kroll et al. |
| 6,263,241 B1 | | 7/2001 | Rosborough et al. |
| 6,298,267 B1 | | 10/2001 | Rosborough et al. |
| 6,314,319 B1 | | 11/2001 | Kroll et al. |
| 6,438,419 B1 | | 8/2002 | Callaway et al. |
| 6,556,865 B2 | | 4/2003 | Walcott et al. |
| 6,577,102 B1 | | 6/2003 | Vaisnys et al. |
| 6,760,621 B2 | | 7/2004 | Walcott et al. |
| 6,853,859 B1 | | 2/2005 | Kroll et al. |
| 7,011,637 B2 | | 3/2006 | Sherman et al. |
| 2002/0156503 A1 | | 10/2002 | Powers et al. |
| 2002/0161407 A1 | | 10/2002 | Walcott et al. |
| 2004/0039313 A1 | | 2/2004 | Sherman et al. |
| 2006/0142809 A1 | | 6/2006 | Kroll et al. |

FOREIGN PATENT DOCUMENTS

| | | |
|---|---|---|
| WO | WO 93/01861 | 2/1993 |
| WO | WO 93/06866 | 4/1993 |
| WO | WO 93/06886 | 4/1993 |
| WO | WO 93/19809 | 10/1993 |
| WO | WO 97/15351 | 5/1997 |
| WO | WO 99/03534 | 1/1999 |

OTHER PUBLICATIONS

"Comparison of Magnetic and Electrical Phrenic Nerve Stimulation in Assessment of Diaphragmatic Contractility," F. Laghi, M.J. Harrison, M.J. Tobin, Applied Physiology, vol. 80, No. 5, pp. 1731-1742, 1996.

"Pacemakers and Electrical Therapy During Advanced Cardiac Life Support," T.P. Aufderheide, M.D., Respiratory Care, vol. 40, No. 4, Apr. 1995.

"Ventricular Defibrillation With Double Square Pulse," J.E.W.B. Kugelberg, Med. & Biology Engineering, vol. 6, pp. 167-169, 1968.

"Ventricular Defibrillation With Single and Twin Pulses of Half-Sinusoidal Current," L.A. Geddes et al., Journal of Applied Physiology, vol. 34, No. 1, Jan. 1973.

"Pacing and Clinical Electrophysiology," S. Furman, PACE, vol. 23, Part II, Apr. 2000.

"Twenty Years of Experience in Phrenic Nerve Stimulation to Pace the Diaphragm," W.W.L. Glenn et al., PACE, vol. 9, Part I, Nov./Dec. 1986.

"Electrical Induction of Ventricular Fibrillation of Resuscitation from Postcountershock Pulseless and Asystolic Cardiac Arrests," C.T. Leng, M.D. et al., Circulation, pp. 723-728, Aug. 7, 2001.

"Need for Sedation in a Patient Undergoing Active Compression-Decompression Cardiopulmonary Resuscitation," J.V. Quinn, M.D., et al. Academic Emergency Medicine, vol. 1, No. 5, Sep./Oct. 1994.

"Comparison of Adrenergic Agonists for the Treatment of Ventricular Fibrillation and Pulseless Electrical Activity," B.E. Bleske, J.E. Billi, Resuscitation 28, pp. 239-251, 1994.

"Resuscitation Time Limits in Experimental Pulseless Electrical Activity Cardiac Arrest Using Cardiopulmonary Bypass," D. DeBehnke, Resuscitation 27, pp. 221-229, 1994.

"Ventricular Defibrillation by Monophasic Trapezoidal-shaped Double-pulses of Low Electrical Energy," L. Resnekov et al., Cardiovascular Resuscitation 3, pp. 261-264, 1968.

"Regional Entrainment of Atrial Fibrillation Studied by High-Resolution Mapping in Open-Chest Dogs," C. Kircfhof, M.D. et al., Circulation, vol. 38, No. 2, pp. 736-748, Aug. 1993.

"Transthoracic Ventricular Defibrillation in the Dog with Unidirectional Rectangular Double Pulses," J.C. Schuder et al., Cardiovascular Research, pp. 497-501, 1970.

"Regional Capture of Fibrillating Right Ventricular Myocardium: Evidence of an Excitable Gap in VG Using High Resolution Cardiac Mapping," B.H. KenKnight et al., JACC, Feb. 1994: 1A-484A.

"Electrically Produced Artificial Ventilation," L.A. Geddes et al., Perspective and Progress, vol. 22, No. 5, pp. 263-271, not dated.

"Ventricular Defibrillation—A New Aspect," J. Kugelberg, ACTA Chirurgica Scandinavica, Supplementum 372, 1967.

"The Effect of an Unsuccessful Subthreshold Shock on the Energy Requirement for the Subsequent Defibrillation," Y. Murakawa et al., American Heart Journal, May 1989.

European Search Report for European Application No. EP 05 85 2106 dated Oct. 28, 2008.

Abstract, Aufderheide TP, et al., "Death by hyperventilation: A common and life threatening problem during cardiopulmonary resuscitation." Wolf Creek VII, Ranch Mirage, CA Jun. 13-16, 2003.

Abstract, Berg, RA et al., "Precountershock cardiopulmonary resuscitation improves ventricular fibrillation median frequency and myocardial readiness for successful defibrillation from prolonged ventricular fibrillation: a randomized, controlled swine study." Ann E.

Cobb LA, et al., "Influence of cardiopulmonary resuscitation prior to defibrillation in patients with out-of-hospital ventricular fibrillation." JAMA Apr. 7, 1999; 281(13): 1182-8.

Eftestol T, et al., "Effects of interrupting precordial compressions on the calculated probability of defibrillation success during out-of-hospital cardiac arrest," Circulation May 14, 2002; 105(19): 2270-3.

Mr. Fell's Electrical Machine described, Gentleman's Magazine, Apr. 2, 1792.

Gilman, Byron et al., "Electrically Induced Chest Constrictions During Ventricular Fibrillation Produce Blood Flow," ACC, Mar. 26, 2007, Presentation #1019-195, 2 pages.

Gilman, Byron et al., "Electrically Induced Chest Constrictions Produce Blood Flow During Ventricular Fibrillation Via Thoracic-Only Pump Mechanism," HRS, May 9, 2007, 2 pages.

Gilman, Byron et al., "Intracardiac Stimulation Produces Blood Flow During Ventricular Fibrillation," Cardiostim, Jun. 2008, 1 page.

Gilman, Byron et al., "Medium Voltage Therapy Produces Blood Flow for Prolonged Duration after Brief VF," HRS, May 2008, 2 pages.

Idris AH, et al., "Effect of ventilation on resuscitation in an animal model of cardiac arrest," Circulation Dec., 1994; 90(6): 3063-9.

KenKnight, Bruce H., et al. "Regional Capture of Fibrillating Ventricular Myocardium: Evidence of an Excitable Gap." Circulation Research, vol. 77, No. 4, Oct. 1995.

Abstract, MacDonald RD, et al., "Impact of prompt defibrillation on cardiac arrest at a major international airport," Prehosp Emerg Care 2002; 6: 1-5.

Abstract, Menegazzi, JJ et al., "Immediate defibrillation versus interventions first in a swine model of prolonged ventricular fibrillation," Resuscitation Nov., 2003; 59(2): 261-70.

Menegazzi, JJ et al., "Ventricular fibrillation scaling exponent can guide timing of defibrillation and other therapies," Circulation Feb. 24, 2004; 109(7): 926-31.

Murdock et al., "Augmentation of Cardiac Output by External Cardiac Pacing: Pacemaker-Induced CPR," Pacing and Clinical Electrophysiology, Jan. 1986, vol. 9, No. 1, Part 1, pp. 1-154.

Abstract, Niemann, JT et al., "Immediate countershock versus cardiopulmonary resuscitation before countershock in a 5-minute swine model of ventricular fibrillation arrest." Ann Emerg Med Dec. 2000; 36(6): 543-6.

Paradis, NA, et al., "Coronary perfusion pressure and the return of spontaneous circulation in human cardiopulmonary resuscitation," J Am Med Assoc 1990; 263: 1106-13.

Rosborough JP et al., "Electrical therapy for post defibrillatory pulseless electrical activity." PACE 2000 (NASPE abstracts) p. 591.

Abstract, Sherman, LD, et al., "Ventricular fibrillation exhibits dynamical properties and self-similarity," Resuscitation 2000; 47: 163-73.

Abstract, Steen, S et al., "The critical importance of minimal delay between chest compressions and subsequent defibrillation: a haemodynamic explanation." Resuscitation Sep. 2003; 58(3): 249-58.

Abstract, Stotz M, et al., "EMS defibrillation-first policy may not improve outcome in out-of-hospital cardiac arrest, " Resuscitation 2003; 58: 277-82.

Valenzuela, TD, et al., "Outcomes of rapid defibrillation by security officers after cardiac arrests in casinos." N Engl J Med 2000; 343: 1206-9.

van Alem AP, et al., "Interruption of cardiopulmonary resuscitation with the use of the automated external defibrillator in out-of-hospital cardiac arrest," Ann Emerg Med Oct. 2003; 42(4): 449-57.

Walcott GP et al., "Effects of burst stimulation during ventricular fibrillation on cardiac function after defibrillation." Am J Physiol Heart Circ Physiol Aug. 2003; 285(2): H766-74.

Wang, HF, et al., "Effects of biphasic vs. monophasic defibrillation on the scaling exponent in a swine model of prolonged ventricular fibrillation," Acad Emerg Med 2001; 8: 771-780.

Wang, Hao MD et al., "Electrically Induced Chest Constrictions Produce Ventilation as Well as Cardiac Output," NAEMSP, Jan. 2008, 3 pages.

Wang, Hao MD et al., "Transthoracic Application of Medium Voltage Therapy for Treatment of Cardiac Arrest," AHA, Nov. 2007, 2 pages.

Wik, L et al., "Delaying defibrillation to give basic cardiopulmonary resuscitation to patients with out-of-hospital ventricular fibrillation: a randomized trial," JAMA Mar. 19, 2003; 289(11): 1389-95.

Abstract, Xie, J, et al., "Spontaneous gasping generates cardiac output during cardiac arrest," Crit Care Med Jan., 2004: 32(1): 238-40.

File Wrapper for U.S. Appl. No. 08/754,712 filed Dec. 6, 1996.
File Wrapper for U.S. Appl. No. 09/139,822 filed Aug. 25, 1998.
File Wrapper for U.S. Appl. No. 09/251,553 filed Feb. 17, 1999.
File Wrapper for U.S. Appl. No. 09/277,311 filed Mar. 26, 1999.
File Wrapper for U.S. Appl. No. 09/694,111 filed May 20, 2003.
File Wrapper for U.S. Appl. No. 09/693,455 filed Oct. 20, 2000.
File Wrapper for U.S. Appl. No. 09/393,443 filed Sep. 8, 1999.
File Wrapper for U.S. Appl. No. 09/392,233 filed Sep. 8, 1999.
File Wrapper for U.S. Appl. No. 08/931,233 filed Sep. 15, 1997.
File Wrapper for U.S. Appl. No. 08/548,013 filed Oct. 25, 1995.
File Wrapper for U.S. Appl. No. 08/548,014 filed Oct. 25, 1995.
File Wrapper for U.S. Appl. No. 08/548,234 filed Oct. 25, 1995.
File Wrapper for U.S. Appl. No. 09/139,316 filed Oct. 25, 1995.
File Wrapper for U.S. Appl. No. 61/056,375 filed May 27, 2008.
File Wrapper for U.S. Appl. No. 60/630,993 filed Nov. 24, 2004.
File Wrapper for U.S. Appl. No. 11/285,756 filed Nov. 22, 2005.
File Wrapper for U.S. Appl. No. 09/693,551 filed Oct. 20, 2000.
File Wrapper for U.S. Appl. No. 11/053,177 filed Feb. 8, 2005.
File Wrapper for U.S. Appl. No. 60/099,458 filed Sep. 8, 1998.
File Wrapper for U.S. Appl. No. 60/099,398 filed Sep. 8, 1998.

Koster, Limited 'hands-off' periods during resuscitation. 2003. pp. 275-276.

Snyder, "Wide variation in cardiopulmonary resuscitation interruption intervals amoung commercially available automated external defibrillators may affect survival despite high defibrillation efficacy", 2004. vol. 32, No. 9. pp. S421-S424.

Wik, ScienceDirect. copyright 2003 pp. 1-6.

* cited by examiner

METHOD AND APPARATUS FOR ELECTRICALLY FORCING CARDIAC OUTPUT IN AN ARRHYTHMIA PATIENT

This application is a continuation of commonly assigned patent application entitled External Electrical Resuscitation Method and Apparatus, Ser. No. 09/693,455, filed Oct. 20, 2000 now U.S. Pat. No. 6,560,484, which in turn is a continuation application of Ser. No. 09/277,311, filed on Mar. 26, 1999, now U.S. Pat. No. 6,185,457, issued Feb. 6, 2001, which is in turn a continuation-in-part application of Ser. No. 08/754,712, filed on Dec. 6, 1996, now U.S. Pat. No. 5,978,703, issued Nov. 2, 1999, which is a continuation application of Ser. No. 08/543,001, filed Oct. 13, 1995, now abandoned, which is in turn a FWC of application Ser. No. 08/251,349, filed May 31, 1994, now abandoned.

BACKGROUND OF THE INVENTION

1. Field of the Invention

The invention relates to the field of therapies for cardiac arrhythmias, and more particularly, to a method and an apparatus for forcing cardiac output by delivering a pulsatile electrical field to the heart during fibrillation of a hemodynamically compromising tachycardia.

2. Background Information

Approximately 400,000 Americans succumb to ventricular fibrillation each year. It is known that ventricular fibrillation, a usually fatal heart arrhythmia, can only be terminated by the application of an electrical shock delivered to the heart. This is through electrodes applied to the chest connected to an external defibrillator or electrodes implanted within the body connected to an implantable cardioverter defibrillator (ICD). Paramedics cannot usually respond rapidly enough with their external defibrillators to restore life. New methods of dealing with this problem include less expensive external defibrillators (and thus more readily available) and smaller implantable defibrillators. Since the first use on humans of a completely implantable cardiac defibrillator in 1980, research has focused on making them continually smaller and more efficient by reducing the defibrillation threshold energy level. The goal has been to reduce the size of the implantable device so that it could be implanted prophylactically, I.E., in high risk patients before an episode of ventricular fibrillation.

An ICD includes an electrical pulse generator and an arrhythmia detection circuit coupled to the heart by a series of two or more electrodes implanted in the body. A battery power supply, and one or more charge storage capacitors are used for delivering defibrillation shocks in the form of electrical current pulses to the heart. These devices try to restore normal rhythm from the fibrillation. While it works well at restoring normal function, the ICD is large in size and not practical for a truly prophylactic device. A small device capable of maintaining minimal cardiac output, in high risk patients, prior to admission into an emergency room is needed.

In addition, external defibrillators are limited in their performance. The typical paramedic defibrillation may be delayed by 10 minutes. At this time defibrillation may be irrelevant since the rhythm is often advanced to asystole. In asystole, there is little or no electrical activity and certainly no cardiac pumping.

There is a need for a new method and apparatus for dealing with ventricular fibrillation. The defibrillation approach does not work satisfactorily. External devices are too slow in arrival and implantable defibrillators are excessively large (and expensive) for prophylactic use.

SUMMARY OF THE INVENTION

The invention provides an electrial method of stimulating cardiac cells causing contraction to force hemodynamic output during fibrillation, hemodynamically compromising tachycardia, or asystole. Forcing fields are applied to the heart to give cardiac output on an emergency basis until the arrhythmia ceases or other intervention takes place. The device is usable as a stand alone external or internal device or as a backup to an ICD, atrial defibrillator, or an antitachycardia pacemaker.

The goal of the invention is maintaining some cardiac output and not necessarily defibrillation. The method is referred to as Electrical Cardiac Output Forcing and the apparatus is the Electrical Cardiac Output Forcer (ECOF).

In the implantable embodiment, a forcing field is generated by applying approximately 50 volts to the heart at a rate of approximately 100-180 beats per minute. These fields are applied after detection of an arrhythmia and maintained for up to several hours. This will generate a cardiac output which is a fraction of the normal maximum capacity. The heart has a 4 or 5 times reserve capacity so a fraction of normal pumping activity will maintain life and consciousness.

The implantable embodiment is implanted in high risk patients who have never had fibrillation. If they do fibrillate, the ECOF device forces a cardiac output for a period of up to several hours, thus giving the patient enough time to get to a hospital. That patient would then be a candidate for an implantable cardioverter defibrillator (ICD). The ECOF differs from the ICD in that it is primarily intended for a single usage in forcing cardiac output over a period of hours, while the ICD is designed to furnish hundreds of defibrillation shocks over a period of years.

Insofar as is known, no prior attempts have been made at forcing pulses during any type of fibrillation. Some workers in the field have experimented for research purposes with local pacing during fibrillation. For example, Kirchhof did local pacing during atrial fibrillation in dog hearts (Circulation 1993; 88: 736-749). He used 0.5 mm diameter electrodes and pacing stimuli. As expected, small areas around the heart were captured but no pumping action was expected or detected. Similar results have been obtained in the ventricle by Ken Knight (Journal of the American College of Cardiology 1994; 283A).

Various researchers have tried multiple pulse defibrillation without success in reducing the energy thresholds, for example, Schuder (Cardiovascular Research; 1970, 4, 497-501), Kugelberg (Medical & Biological Engineering; 1968, 6, 167-169 and Acta Chirurgica Scandinavia; 1967, 372), Resnekov (Cardiovascular Research; 1968, 2, 261-264), and Geddes (Journal of Applied Physiology; 1973, 34, 8-11).

More recently, Sweeney (U.S. Pat. No. 4,996,984) has experimented with multiple (primarily dual) shocks of timing calculated from the fibrillation rate. None of these approaches has been able to significantly reduce voltages from conventional defibrillation shocks. Importantly, none of these approaches anticipated the idea that the individual pulses might force cardiac output or could sustain life indefinitely.

Some have considered the use of smaller pulses, before the shock, to reduce the energy required for a defibrillation shock (Kroll, European Application No. 540266), but never anticipated eliminating the defibrillation shock itself or anticipated that the pulses themselves could maintain cardiac output. Some have suggested using higher voltage pulses to terminate ventricular tachycardias, but no suggestion was made of an application with fibrillation or of obtaining cardiac output (Kroll WO 93/19809) and Duffin (WO 93/06886).

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, applicants provide these embodiments so that this disclosure will be thorough and complete, and will convey the scope of the invention to those skilled in the art.

Figure 1:
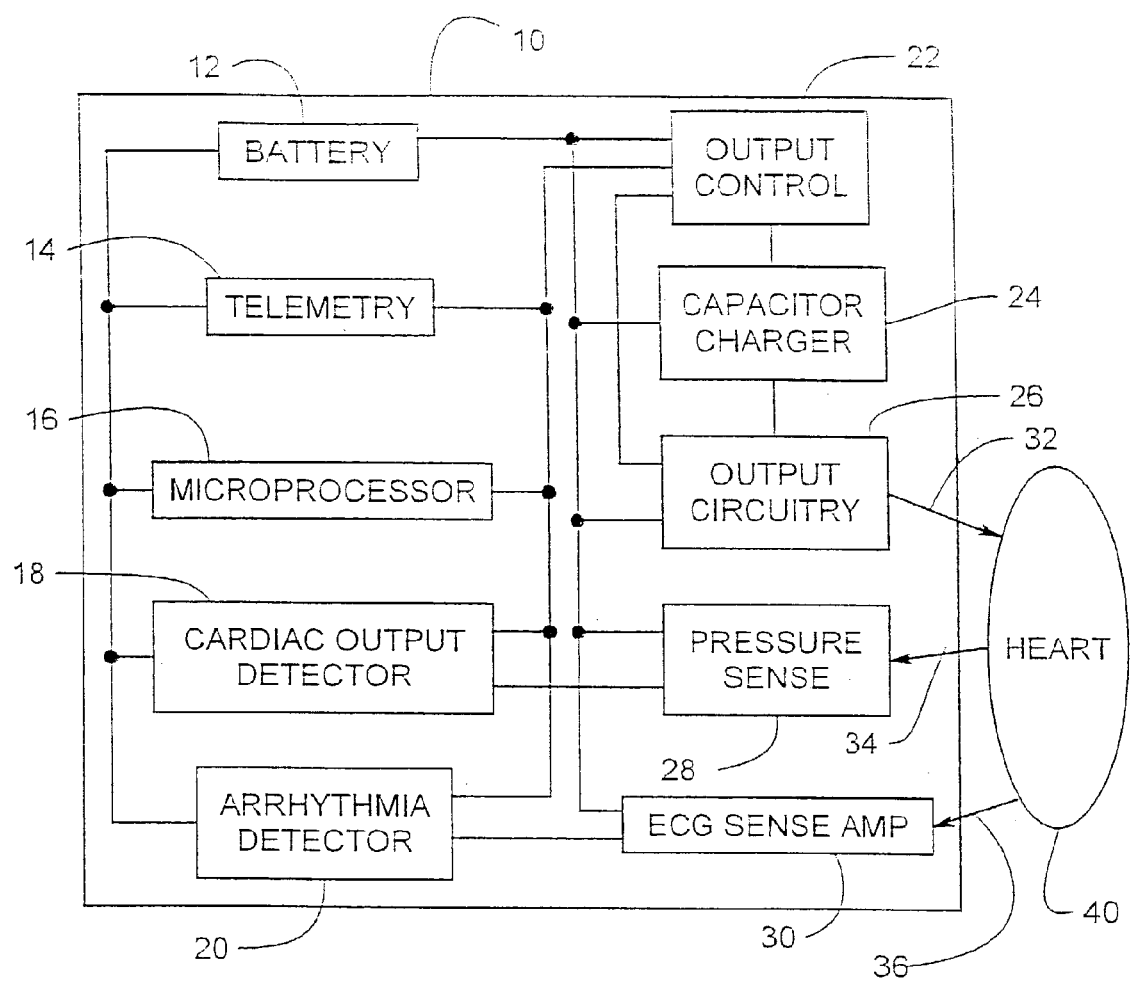
FIG. 1 is a block diagram illustrating a system constructed in accordance with the principles of the present invention.

FIG. 1 is a block diagram illustrating a system 10 constructed in accordance with the principles of the present invention. The device circuitry is connected to the heart 40 via a series of leads; output lead 32, pressure sense lead 34, and ECG sense lead 36. The electronic circuit includes a conventional ECG amplifier 30 for amplifying cardiac signals. The amplified cardiac signals are analyzed by a conventional arrhythmia detector 20 which determines if an arrhythmia is present. The arrhythmia detector 20 may be one of several types well known to those skilled in the art and is preferably able to distinguish between different types of arrhythmias. For example; fibrillation, tachycardia or asystole. The circuit also contains an optional pressure sensing section 28 which amplifies and conditions a signal from an optional pressure sensor from within the heart or artery. The output of the pressure sense circuit 28 is fed to a cardiac output detection circuit 18 which analyzes the data and determines an estimate of the cardiac output. Data from the arrhythmia detector circuit 20 and the cardiac output detection circuit 18 is fed to the microprocessor 16. The microprocessor 16 determines if Electrical Cardiac Output Forcing (ECOF) is appropriate. If forcing is indicated, the microprocessor 16 prompts the output control 22 to charge a capacitor within the output circuit 26 via the capacitor charger 24. The output control 22 directs the output circuitry 26 to deliver the pulses to the heart 40 via the output leads 32. The microprocessor 16 may communicate with external sources via a telemetry circuit 14 within the device 10. The power for the device 10 is supplied by an internal battery 12.

Figure 2A:
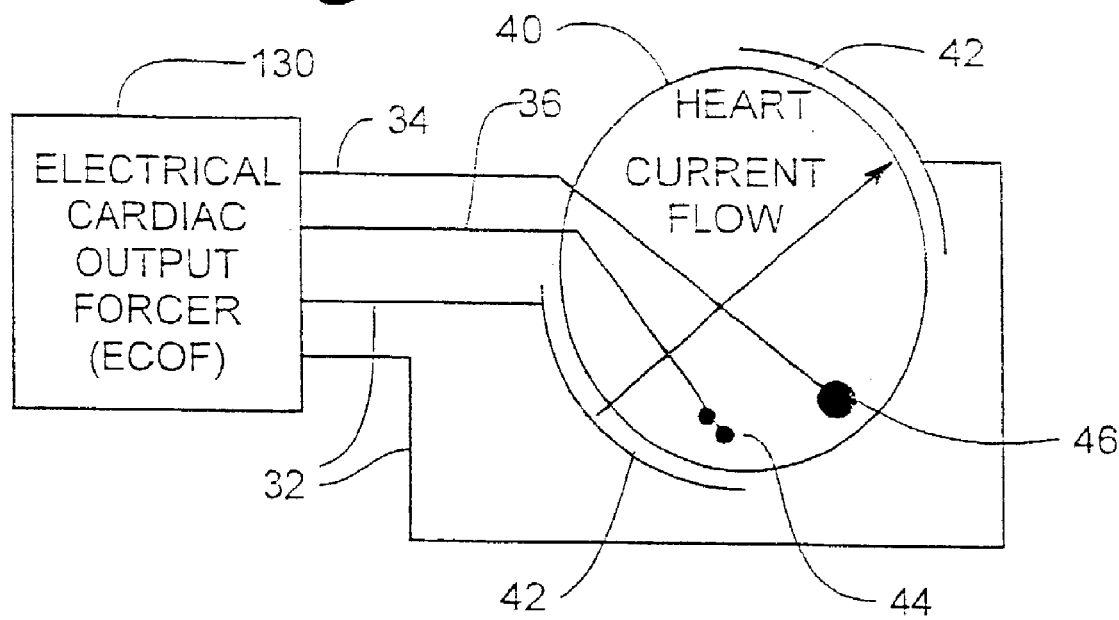
FIG. 2a shows the connection of an implantable embodiment of the device to the heart in an epicardial patch configuration.

FIG. 2a is a diagram showing the connection of an implantable embodiment of the device 130 to the heart 40 in an epicardial patch configuration. In this thoracotomy configuration, current passes through an output lead pair 32 to electrode patches 42 which direct the current through the heart 40. There is an optional pressure sense lead 34 which passes the signal from an optional pressure transducer 46 which lies in the heart 40. The ECG is monitored by sense electrodes 44 and passed to the device 130 by a lead 36. The area of the electrodes 42 is at least 0.5 cm$^2$. The size of the electrode is greater than that of a pacing lead and no more than that of a defibrillation electrode or between approximately 0.5 cm$^2$ and 20 cm$^2$ each.

Figure 2B:
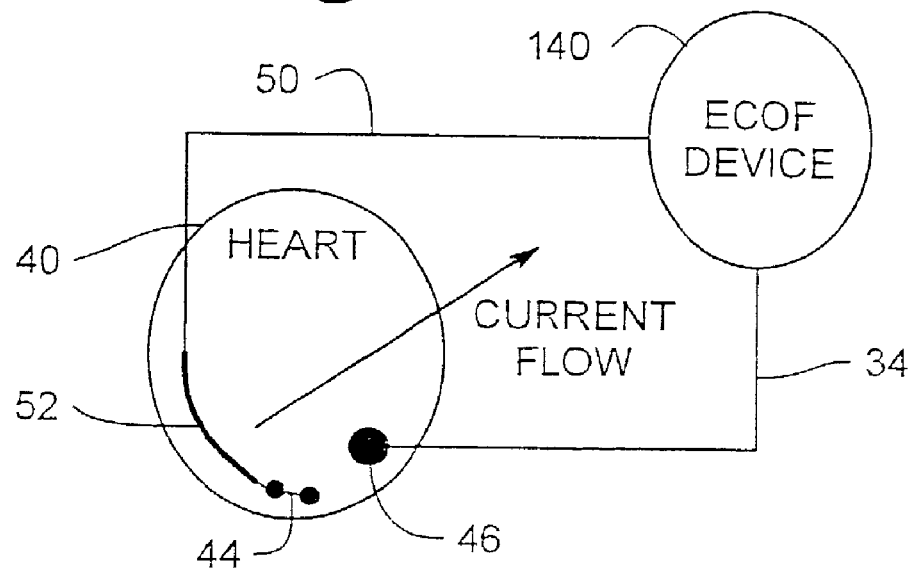
FIG. 2b shows the connection of an implantable embodiment of the device to the heart using an endocardial lead system and the device housing as an electrode.

FIG. 2b shows a non-thoracotomy system embodiment of the invention. In this system, the current passes from a coil electrode 52 in the heart 40 to the housing of the device 140. An endocardial lead 50 combines the ECG sensing lead and the pulse output lead. The ECG is monitored by sense electrodes 44 in the heart 40 and passes through the endocardial lead 50. There is an optional pressure transducer 46 in the heart 40 which passes a signal to the device 140 via optional lead 34.

Figure 3A:
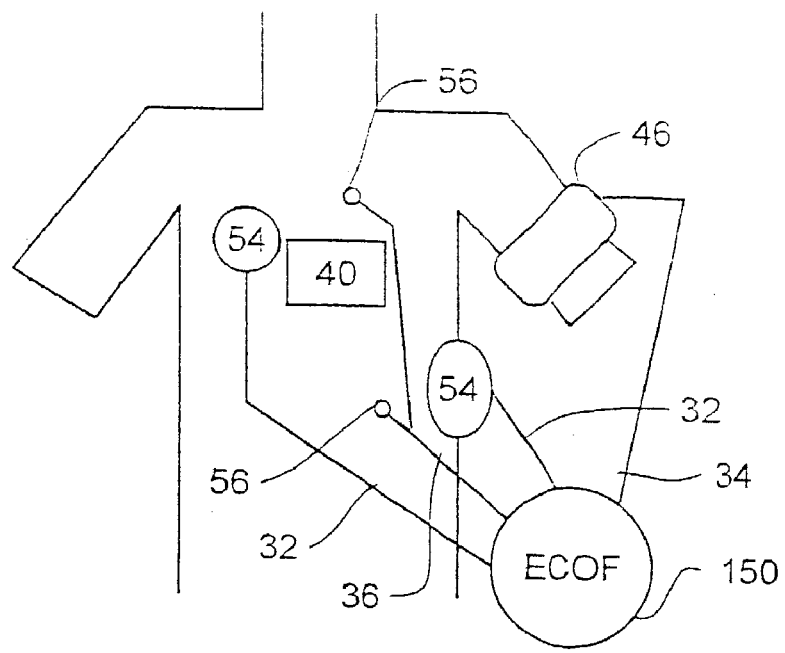
FIG. 3a shows the connection of an external embodiment of the invention.

FIG. 3a shows an external embodiment of the invention. External patch electrodes 54 are placed on the chest to deliver current to the heart 40 through output lead 32. The ECG is monitored by surface electrodes 56 and passed to the device 150 by a lead 36. Alternately, the ECG could be monitored by the external patch electrodes 54. An optional pressure sensor 46 passes a pressure signal via an optional pressure sense lead 34. This embodiment could be used as a substitute (due to its small size) for an external defibrillator and keep a patient alive until arrival at a hospital. Also, the system could precede the external defibrillator by generating output in patients in asystole until blood flow and rhythm are restored.

Figure 3B:
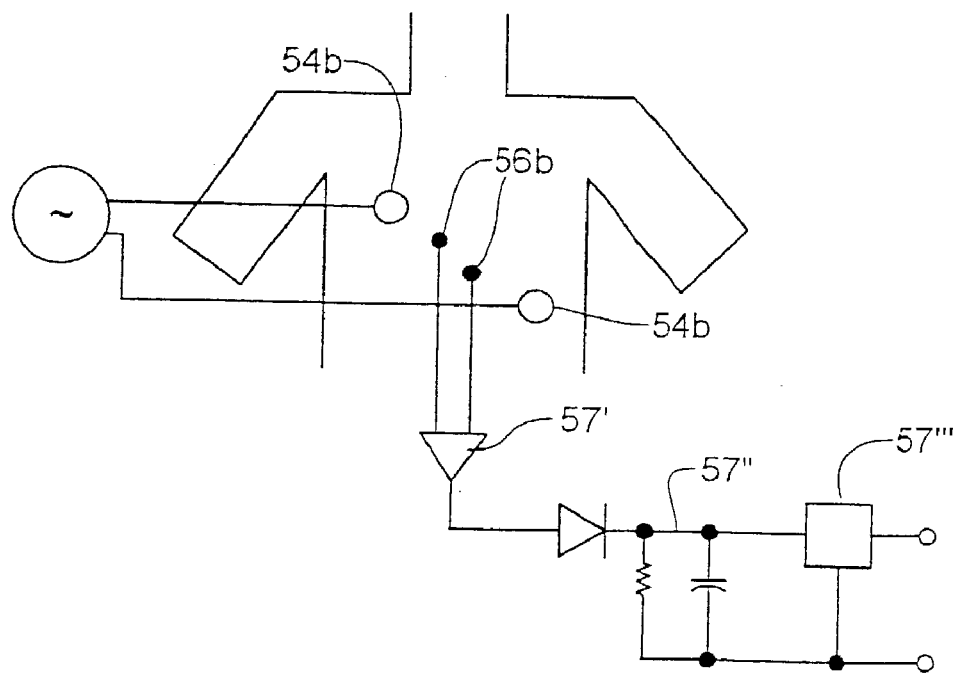
FIG. 3b shows a representative cardiac output detection configuration.

FIG. 3b shows another means of detecting cardiac output which may be useful to the external embodiment, in particular, of this invention. FIG. 3b illustrates use of a relatively high frequency (such as about 10-50 kHz) impedance measurement across the chest area of the patient, with either 2 or more electrodes, for example patch electrodes 54b. Surface electrodes 56b sense and deliver the signal, which may be rectified to highlight the cardiac mechanical frequencies (1-10 Hz) at amplifier 57'. In one embodiment, this may be a 30 kHz selective amplifier. Processing circuitry may further include rectifier means 57" and filter 57'", which could include a 1-20 Hz filter or similar filter means.

Figure 4:
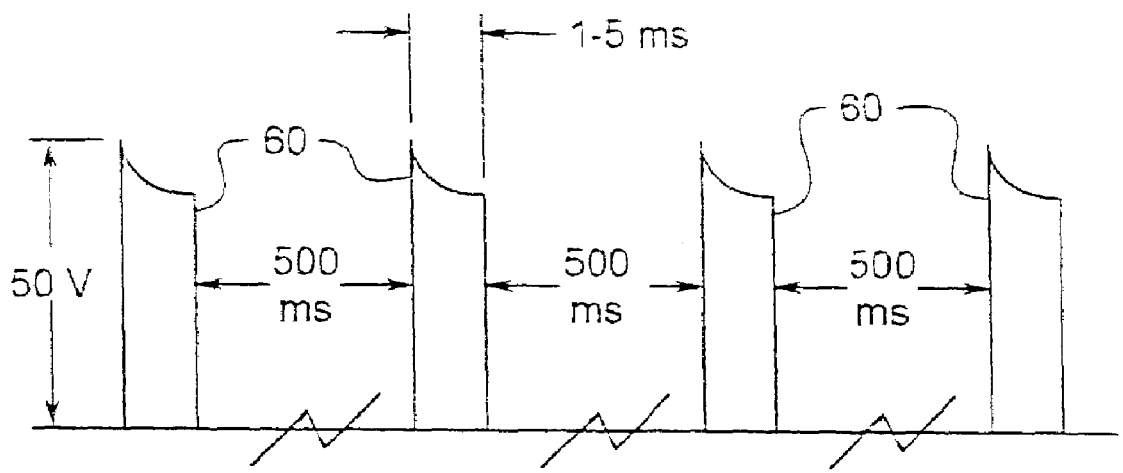
FIG. 4 is a diagram showing a representative pulsatile electrical signal.

A series of forcing pulses 60 are shown in FIG. 4. The pulses are approximately 50 V in amplitude with a spacing of approximately 500 ms. The 50 V and the 500 ms pulse spacing are chosen as illustrative for an implantable embodiment. The forcing pulse interval is chosen to maximize cardiac output within the limits of device circuitry and the response of the heart muscle. An interval of 500 ms corresponds to a heart rate of 120 beats per minute. This will produce a greater output than a typical resting rate of 60 beats per minute. However, a rate of 240 beats per minute would produce a lower output due to mechanical limitations of the heart. Thus a practical range is 60 to 200 beats per minute is appropriate. The pulses could also be timed to coincide with the natural pumping of the atria, thus improving overall cardiac output.

The higher voltage, the higher the forcing fields, and therefore a greater number of heart cells contracting producing greater cardiac output. However, the higher voltage produces greater patient discomfort and extraneous muscle twitching.

Implantable batteries are also limited to a certain power output and energy storage. If an output pulse is 50 V and the electrode impedance is 50 Ω, the power during the pulse is $P=V^2/R=50V*50V/50\Omega=50W$. If the pulse has a duration of 2 ms then the energy per pulse is 0.1 J. If two pulses are delivered every second, the charger must be capable of delivering 0.2 J per second which is 200 mW. This is well within the limits of an implantable battery. An implantable battery can typically deliver 5 W of power. However, 200 V pulses at 3 per second would require 4.8 W which is near the limit of the battery and charging circuitry. A typical implantable battery energy capacity is 10,000 J. Delivering forcing pulses at a rate of 4.8 W would deplete the battery in only 35 minutes (10,000 J/4.8W=2083 seconds). Thirty five minutes may not be enough time to transport the patient to a hospital. Therefore 200 V represents the highest practical voltage for continuous operation in an implantable embodiment, although voltages of up to 350 V could be used for short periods and adjusted down when hemodynamic output is verified. A practical lower limit is about 10 A. During normal sinus rhythm, 10 V delivered through the patches would pace. However, during fibrillation the 10 V could not pace and only cells very near the electrodes would be captured. This would be insufficient for forcing cardiac output.

These calculations also suggest other differences between an implantable ECOF and an ICD. With a battery storing 10,000 J and ECOF pulse having 0.1 J, this ECOF would be capable of delivering 100,000 pulses. An ICD can only deliver 200-400 shocks of about 30 J. The ECOF is also very different from an implantable pacemaker which typically delivers 150,000,000 pacing pulses (5 years at 60 BPM) each of about 0.00005 J.

For an external ECOF the calculations are similar, but scaled up. The typical ECOF pulse would have a voltage of 100 V with a range of 25-500 V. With electrode impedances of 50 Ω the power during the pulse is $P=V^2/R=100V*100V/50\Omega=200 W$ with a range of 12.5-5,000 W. If the pulse has a duration of 2-5 ms, then the energy per pulse is 0.02-25 J. This is much less than the American Heart Association recommended output of 360 J for an external defibrillator.

This is also different from an external transthoracic pacemaker. These devices are rated by current and typically have an output range of 30-140 mA. Most patients are paced by pulses of 40-70 mA of current. An example of a modern external thoracic pacemaker is given by Freeman in application WO 93/01861. Assuming an electrical impedance of 50Ω and the ECOF voltage range of 25-500 V, then the ECOF current range would be 500 mA 59 10 A. Since electrode impedance increases with lower voltage, the 25 V ECOF pulse would probably see an impedance of 100Ω thereby giving a lower current of 250 mA.

However, it is now recognized that use of external defibrillation has a homogeneous current advantage over ICDs, due to the relatively poor electrical field coverage of the ICDs. Accordingly, it is believed that the external ECOF-type of pulses described herein have an added advantage over pulses delivered with implantable systems. A further advantage of external delivery of pulses exists with regard to the potential for skeletal muscle and diaphragm contraction to assist with cardiac output. This type of contraction augments the cardiac contraction normally attributed to both implanted and external pulse delivery. These advantages accumulate to present an external ECOF ratio which allows for use of voltage levels between a range of about 20-2000 volts in a combined external ECOF and defibrillation device. However, without the traditional higher voltage defibrillation requirement, it is likely that an external ECOF-type device may only require a delivery capability of between about 20-1000 volts, with possible initial capture pulses that may be higher or lower than that upper range. For example, if an external ECOF-type ratio is no longer considered to be between 5-10, and is only assigned a value of 2, then the 10 volt internal minimum becomes a 20 volt external minimum, and the internal typical delivery range of 20-200 volts becomes a typical external delivery range of 40-400 volts. In similar manner, a representative value for a maximum internal delivery of an ECOF-type pulse might be 350 V, with a comparable external value being only 700 V using this ratio. When considered in the context of being a non-invasive therapy, the external ECOF-type of application is quite advantageous and energy efficient. This is particularly so in view of the unexpected ratio described above which is improved over the previous known ratios of AED/ICD voltage ratio values of between about 4-10.

Figure 5:
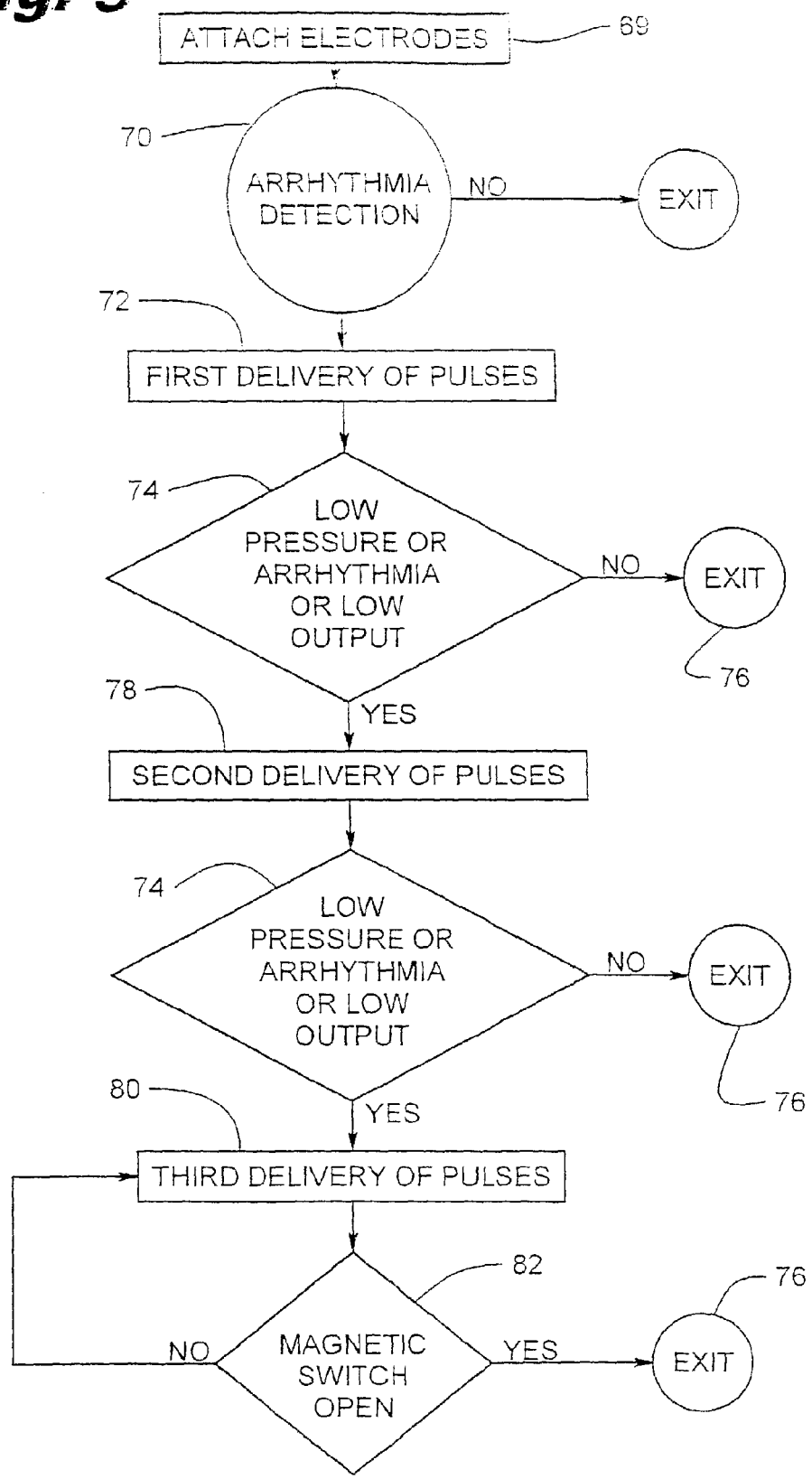
FIG. 5 is a flowchart illustrating one embodiment of the method of the invention.

FIG. 5 is a flowchart illustrating the method of the invention, which is provided for purposes of illustration only. One skilled in the art will recognize from the discussion that alternative embodiments may be employed without departing from the principles of the invention. The flow diagram shown in FIG. 5 represents a method of automatically treating a heart which is in fibrillation, tachycardia, or asystole and thereby pumping inefficiently or not at all. Electrodes are attached 69 and diagnoses the presence of an arrhythmia 70. A series of cardiac output forcing electric pulses 72 is automatically delivered. It should be understood that the therapy 72 may be delivered for any output within the ranges stated herein which is appropriate for the particular cardiac dysrhythmia. After delivery of forcing pulses (for example, such as either ten pulses at a rate of 60-200 BPM or a series of pulses for a certain time, e.g., 20 seconds) in the first block 72, the status of the heart is determined 74. If an anomaly such as arrhythmia or low cardiac output is still present and/or there exists low pressure within the heart, more forcing pulses are delivered 78. Such delivery may include, for example, perhaps 100 pulses of 200 V for 20 seconds, although these values may be varied according to the recipient's condition. If the heart is pumping at a safe level, the therapy ceases and exits 76. Note that this means that the ECOF successfully defibrillated the patient's heart even though this may not be the only goal of this therapy. This could be tested in patients who were scheduled to receive an ICD, in a hospital setting. Those patients who are defibrillated by ECOF pulse therapy could then receive the ECOF instead of the larger ICD. After the therapy 78 has been delivered, the pressure and ECG is again monitored 74. If the therapy 78 is successful, it ceases and exits 76. If the therapy 78 is unsuccessful in producing a safe level of pumping efficiency, the method proceeds to a third delivery mode 80 which may comprise a continuous cardiac assist mode, a defibrillate mode, or some combination of the above. Indeed, in one embodiment of the method depicted in FIG. 5, the first step of delivery of pulses is an ECOF-type of pulse sequence, the second step of delivery of pulses is a high voltage defibrillating shock type of pulse, and the third step of delivery of pulses is an assist-type of ECOF-like pulse sequence. In another embodiment of this method, it is possible to deliver a shock level pulse one or several times, then deliver a forcing or ECOF type of pulse sequence one or more times, and then again deliver a shock level pulse one or several times. The inclusion of the forcing pulses between shocks replenishes the blood in the vessels during the therapy.

The therapy may only be stopped by an external command, for example, a telemetry signal or a magnet which is applied to the chest activating a magnetic reed switch 82 which terminates the therapy and exits 76, or some other appropriate termination means is activated. To minimize patient discomfort and maximize battery life, the forcing voltage could be adjusted down when sufficient pressure signals or adequate flow measured by other means were detected, for example, the pressure sense transducer could be replaced by an oxygen detector or a doppler flow measuring device. The pulse rate could also be adjusted to maximize output.

Figure 6:
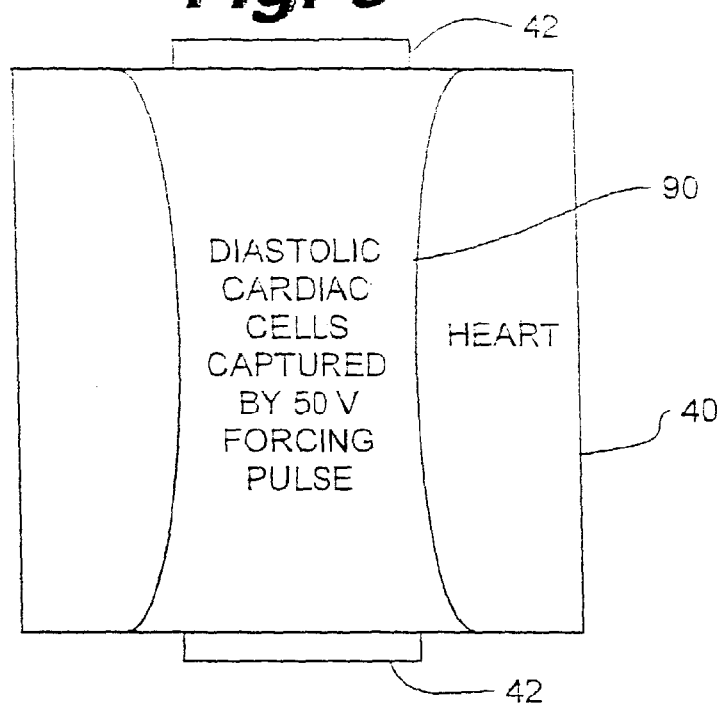
FIG. 6 is a diagram showing the expected effect of a 50 V pulse on the heart during diastole.

FIG. 6 is a diagram showing the effect of a 50 V forcing pulse on the heart 40 during electrical diastole (cells at rest). The current is passed through the heart 40 by the electrodes 42. Approximately 60% of cardiac cells 90 would be captured by a 50 V pulse if the cells were in diastole. The captured cells 90 mostly lie in the direct path between the electrodes 42 and near the electrodes 42 where the field strengths are highest. Of course over a time period of about 100 ms these directly captured cells then propagate an activation wavefront to stimulate the rest of the heart. This so called far-field pacing is irrelevant here as the hearts, of interest, are in fibrillation and not in diastole.

Figure 7:
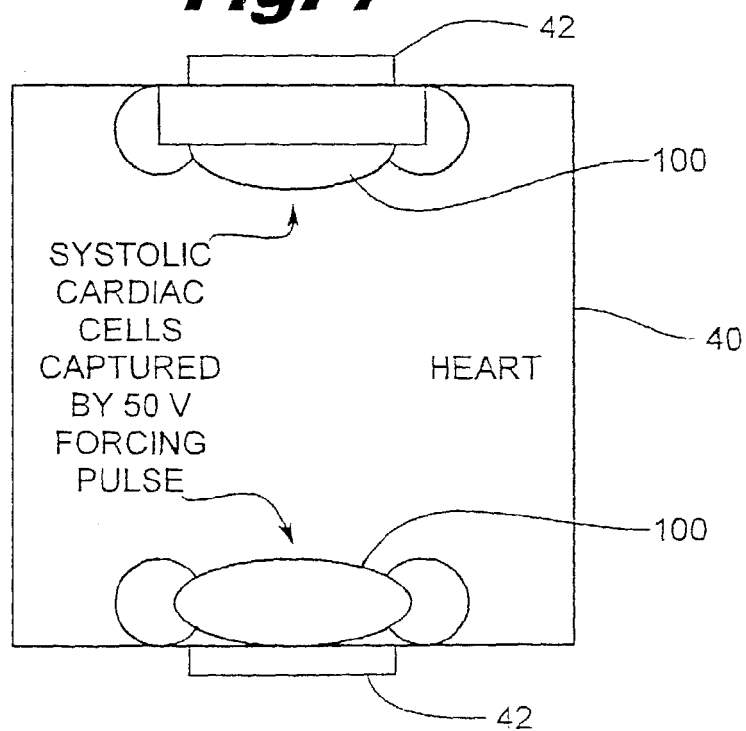
FIG. 7 is a diagram showing the expected effect of a 50 V pulse on the heart during systole.

FIG. 7 is a diagram showing the effect of a 50 V forcing pulse on the heart during electrical systole (cells already stimulated). The current is passed through the heart 40 by the electrodes 42. Approximately 20% of cardiac cells 100 would be captured by a 50 V pulse if the cells were in systole. The captured cells 100 are nearest each electrode 42 where the field strengths are highest. Capture in systolic cells means that their activation potential is extended. This capture requires significantly higher fields (10 V/cm) than those required for diastolic cell capture (1 V/cm).

Figure 8:
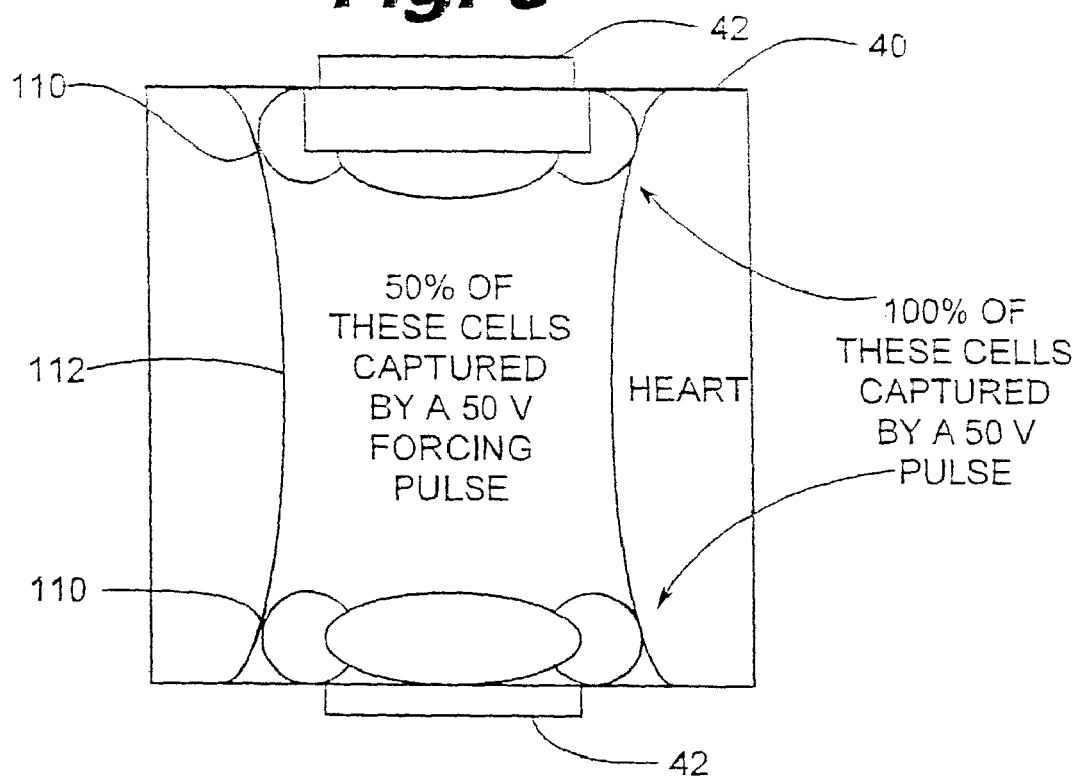
FIG. 8 is a diagram showing the expected effect of a 50 V pulse on the heart during fibrillation.

FIG. 8 is a diagram showing the effect of a 50 V forcing pulse on the heart during fibrillation. During fibrillation there are always cells in systole and diastole simultaneously. But, the vast majority are in systole. This diagram assumes 50% of the cells are in diastole which applies only after several capturing pulses. The current is passed through the heart 40 by the electrodes 42. 100% of the cells 110 nearest the electrodes 42 would be captured due to the high field strength. As shown in FIG. 7, even systolic cells are captured by high field strengths. 50% of the cells 112 in the direct path between the electrodes 42 would be captured if it is assumed that 50% of all cells are in diastole. If roughly 60% of cardiac cells are captured by a 50 V pulse when the cells are in diastole, and 20% are captured when in systole, and if 50% are in systole and 50% in diastole, 40% would be captured during fibrillation. This calculation is shown in the following table. The last two columns give the mechanical action resulting and the contribution to forcing a cardiac output.

Considering the cardiac cells that are originally in diastole, (rows A & B) in the table below, the A row represents the diastolic cells that are not captured by the forcing pulse. If 50% of the heart's cells are in diastole and 40% of those are not captured that is 20% of the total cells. These cells will, however, shortly contract on their own (from previous wavefronts or new ones) providing a positive gain in mechanical action and therefore cardiac output. The B row corresponds to the diastolic cells that are captured. If 60% of the diastolic cells (50% of total) contract due to the forcing field this is 30% of the total heart cells. These cells provide the biggest gain in mechanical action and cardiac output. Next considering the activity of the systolic cells (rows C & D), if 50% of the heart's cells are in systole and 80% of those are not captured (row C), that is 40% of the heart's cells. These cells soon relax and negate a portion of the cardiac output. The systolic cells that are captured (row D) are 10% of the heart's cells (20% of 50%). These cells will hold their contraction and be neutral to cardiac output. The net result is a gain in contraction which forces cardiac output.

| Original status of the cells | Percentage of the cardiac cells | Status of the cardiac cells | Percentage of the original status | Percentage of the total cells | Mechanical Action | Forcing Cardiac Output Effect |
|---|---|---|---|---|---|---|
| (A) Diastolic | 50% | Diastolic non-captured | 40% to 50% | 20% | Will start to contract on own | Positive (+) |
| (B) Diastolic | | Diastolic captured | 60% of 50% | 30% | contract | positive (++) |
| (C) Systolic | 50% | Systolic non-captured | 80% of 50% | 40% | Will start to relax on own | Negative (−) |
| (D) Systolic | | Systolic captured | 20% of 50% | 10% | hold | neutral (0) |
| Total | 100% | | 100% | 100% | More contraction | Positive (++) |

The net result over a 200 ms mechanical response is given in the next table. The major contribution is in row (B) from the captured diastolic cells contracting.

| Row | Status of the Cardiac Cells | Change in Output | Description of Activity |
|---|---|---|---|
| A | Diastolic non-captured | +5% | Positive. Some cells will begin to contract on their own. |
| B | Diastolic captured | +30% | Positive. Cells contract due to forcing field. |
| C | Systolic non-captured | −5% | Negative. Some cells will begin to relax on their own. |
| D | Systolic captured | 0% | Neutral. Cells hold contraction due to forcing field. |

| Row | Status of the Cardiac Cells | Change in Output | Description of Activity |
|---|---|---|---|
| Net Gain | | +30% | A net gain in cardiac output due to forcing fields. |

The 30% net pumping action should be sufficient to maintain survival and consciousness, because the heart has a 4-5 times reserve capacity.

Figure 9A:
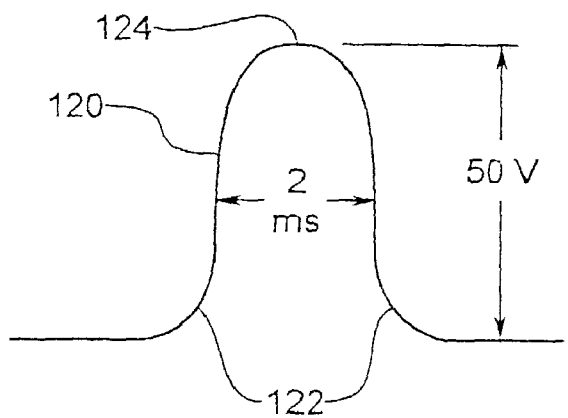
FIGS. 9a and 9b show various waveforms useful for the electrical cardiac output forcing method and apparatus.

FIG. 9 depicts examples of waveforms designed to minimize the twitching of the chest muscles which can be very uncomfortable to the patient. In FIG. 9a is seen a low harmonic pulse waveform 120 which has a very gradual "foot" 122 and a gradual peak 124. Such a pulse has less high frequency energy components and thus is less likely to stimulate the skeletal muscle.

Figure 9B:
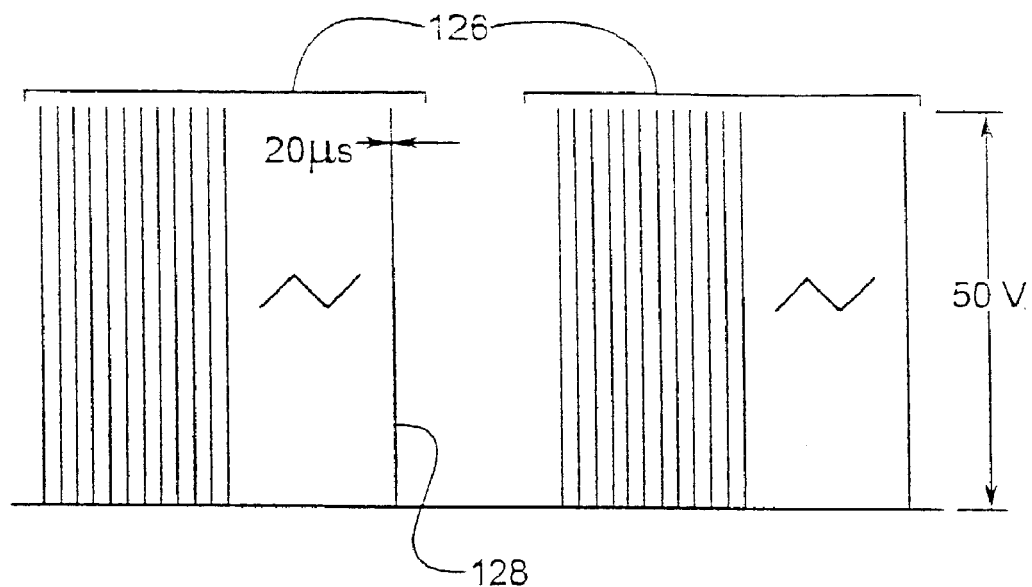

FIG. 9b shows a technique of going to the opposite extreme. Here, each compound forcing pulse 126 is actually composed of 50 very short spikes 128 each of which is 20 µs in width with a 20 µms spacing. The heart will tend to average out these thin pulses and "see" a 2 ms wide forcing pulse. The skeletal muscle, however, is not efficiently stimulated by these extremely narrow pulses. The skeletal muscle will not average out this signal either. This approach could help minimize skeletal muscle twitching and discomfort.

An alternative system would be to charge the capacitor to 300 V for the first pulse to capture many cells therefore putting those cells into diastole after a delay of 100-200 ms. At this point the voltage could be lowered to 100 V and delivered every 100 ms. A 3 watt DC-DC converter with a 67% efficiency could provide 100 ms interval forcing pulses assuming a 50 Ω resistance and 1 ms pulse (0.2 J). This rate is too fast for forcing cardiac output due to mechanical limitations, but is very effective for electrical capture. After sufficient capture, the rate of forcing pulses could be slowed down to 100-170 beats per minute for optimum cardiac output.

The Electrical Cardiac Output Forcing device (ECOF) could also be used to help patients with atrial fibrillation. As an alternative embodiment to the ventricular placement of FIG. 2b, the electrode coil 52 and sensing electrodes 44 could be placed in the atrium. The device could then function to force atrial output. Even though atrial fibrillation is not instantly fatal like ventricular fibrillation is, clots can build up in the atria which can eventually lead to strokes. Cardiac output forcing of the atria on a daily basis may limit this problem. It is also possible that after a number of forcing pulses the atria would return to a normal rhythm. There is however, no urgency as is the case with ventricular fibrillation.

Figure 10:
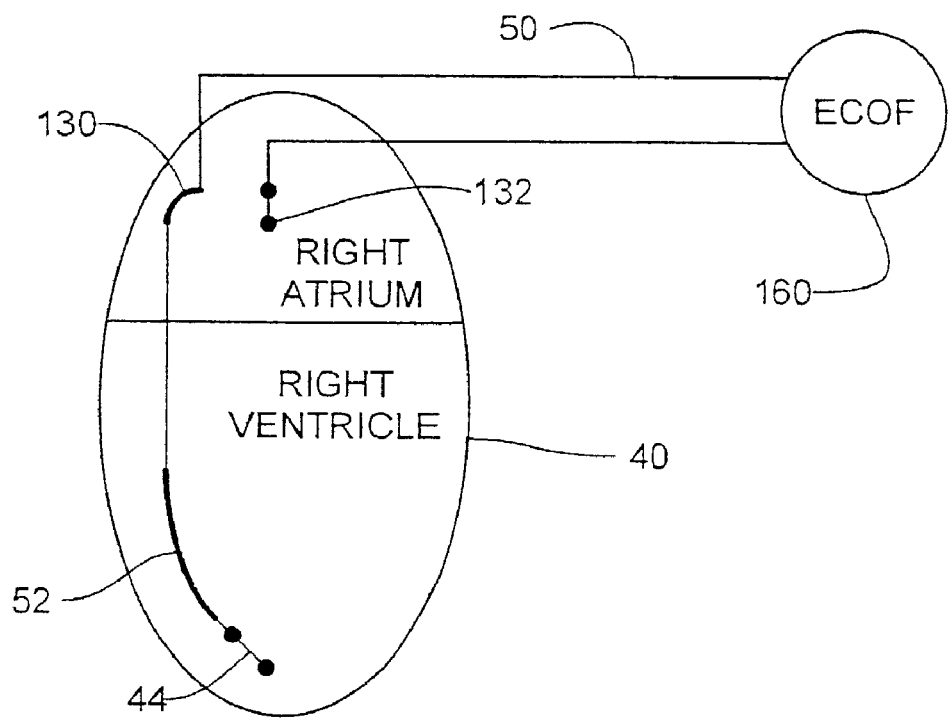
FIG. 10 shows the device used as a backup to an atrial defibrillator.

A second use of this invention for atrial defibrillation is shown in FIG. 10. As before in FIG. 2b, the ECOF 160 is shown connected to the heart 40 via endocardial lead 50. Again forcing coil electrode 52 and sensing electrodes 44 are in the right ventricle. In addition a large atrial coil electrode 130 and atrial sensing electrodes 132 are in the right atrium. These would be used for conventional atrial defibrillation. One of the big concerns with atrial defibrillation is that in a few cases, an atrial defibrillation shock causes ventricular fibrillation. If this happens, the patient dies within minutes. With the ECOF approach, for the left ventricle, one could maintain output in the patient for several hours and thus have enough time for transport to a hospital or external defibrillation. Thus the ECOF approach in the ventricle could provide a safety backup to atrial defibrillation.

Many cardiac patients have no known risk of ventricular fibrillation, but suffer regularly from ventricular tachycardia. Accordingly, these people can be treated with anti-tachycardia pacing (ATP). Unfortunately, occasionally ATP will cause a ventricular fibrillation. Then a large defibrillation shock must be applied. Thus it is not considered safe to implant a pure ATP device and these patients instead receive a full size ICD. The ECOF approach also serves as a safety backup and thus allow the implantation of true ATP devices. The system is depicted in FIG. 2b, although the pressure sensor 46 would typically not be needed.

Low energy cardioverters can also be used to treat ventricular tachycardias. These devices are also not considered safe as stand alone devices due to the fact that they may not terminate the rhythm or that they may cause fibrillation. The ECOF method also could be used as a safety backup thus allowing the implantation of cardioverters without defibrillation capabilities. Such a system is shown in FIG. 2b.

It should be understood that various alternatives to the embodiments of the invention described herein may be employed in practicing the invention. For example, while most of the discussion is in the context of an implantable device, the concepts of the invention are also applicable to external delivery systems. The use of ECOF-type of low voltage forcing pulses allows the choice of optimum therapy for different patient needs while only delivering the minimum voltage necessary to a patient in order to achieve the desired outcome. It is intended that the following claims define the scope of the invention and that structures and methods within the scope of these claims and their equivalents be covered thereby.

What is claimed is:

1. A method for treating an arrhythmia in a patient, comprising the steps of:
   a. attaching a plurality of electrodes to external portions of a patient's body proximate the patient's thoracic region so that the electrodes may deliver electrical pulses which will be transmitted through portions of the patient's upper body;
   b. detecting the presence of arrhythmia in the patient;
   c. delivering non-defibrillatory electrical current pulses through the patient's body via the electrodes after detecting an arrhythmia, the non-defibrillatory electrical current pulses having an amplitude of less than the amplitude of a normal defibrillation shock, and greater than that which would only pace the heart, to force contraction of patient muscle and facilitate a minimum level of cardiac output; and
   d. delivering at least one defibrillation pulse having an amplitude sufficient to defibrillate the patient's heart.

2. The method of claim 1, wherein the arrhythmia is ventricular fibrillation.

3. The method of claim 1, wherein the arrhythmia is ventricular tachycardia.

4. The method of claim 1, wherein the non-defibrillatory electrical current pulses have an amplitude of between 200 and 5000 watts.

5. The method of claim 1, wherein the non-defibrillatory electrical current pulses have an amplitude of between 12.5 and 5000 average watts.

6. The method of claim 1, wherein the non-defibrillatory electrical current pulses have an amplitude of between 100 and 400 volts.

7. The method of claim 1, wherein the non-defibrillatory electrical current pulses have an amplitude of between 100 and 500 volts.

8. The method of claim 1, wherein the non-defibrillatory electrical current pulses have an amplitude of between 100 and 700 volts.

9. The method of claim 1, wherein the non-defibrillatory electrical current pulses have an amplitude of between 100 and 1000 volts.

10. The method of claim 1, wherein the non-defibrillatory electrical current pulses have an amplitude of between 100 and 2000 volts.

11. The method of claim 1, wherein the non-defibrillatory electrical current pulses have an amplitude of between 0.02 and 25 joules.

12. The method of claim 1, wherein the non-defibrillatory electrical current pulses have an amplitude of between 0.25 and 10 amperes.

13. The method of claim 1, wherein the non-defibrillatory electrical current pulses have an amplitude of between 0.5 and 10 amperes.

14. The method of claim 1, wherein the non-defibrillatory electrical current pulses are composed of shorter pulses shorter than the at least one defibrillation pulse.

15. The method of claim 14, wherein the shorter pulses have pulse widths of between 20 us and 2 ms.

16. The method of claim 1, wherein the non-defibrillatory electrical current pulses are composed of at least 10 shorter pulses shorter than the at least one defibrillation pulse.

17. The method of claim 1, wherein the non-defibrillatory electrical current pulses are composed of at most 50 shorter pulses shorter than the at least one defibrillation pulse.

18. The method of claim 1, wherein the step of delivering non-defibrillatory electrical current pulses is administered for a period of less than about 20 seconds.

19. The method of claim 1, wherein the at least one defibrillation pulse has an amplitude of between 25 and 360 joules.

20. A method for treating a tachyarrhythmia in a patient, comprising the steps of:
   a. attaching a plurality of electrodes to external portions of a patient's body proximate the patient's thoracic region so that the electrodes may deliver electrical pulses which will be transmitted through portions of the patient's upper body;
   b. detecting the presence of tachyarrhythmia in the patient;
   c. delivering the non-defibrillatory electrical current pulses through the patient's body via the electrodes after detecting an tachyarrhythmia, the non-defibrillatory electrical current pulses having an amplitude of less than the amplitude of a normal defibrillation shock, and greater than that which would only pace the heart, to force contraction of patient muscle and facilitate a minimum level of cardiac output;
   d. delivering at least one defibrillation pulse having an amplitude sufficient to defibrillate the patient's heart.

21. The method of claim 20, wherein the tachyarrhythmia is ventricular fibrillation.

22. The method of claim 20, wherein the tachyarrhythmia is ventricular tachycardia.

23. The method of claim 20, wherein the non-defibrillatory electrical current pulses have an amplitude of between 200 and 5000 watts.

24. The method of claim 20, wherein the non-defibrillatory electrical current pulses have an amplitude of between 12.5 and 5000 average watts.

25. The method of claim 20, wherein the non-defibrillatory electrical current pulses have an amplitude of between 100 and 400 volts.

26. The method of claim 20, wherein the non-defibrillatory electrical current pulses have an amplitude of between 100 and 500 volts.

27. The method of claim 20, wherein the non-defibrillatory electrical current pulses have an amplitude of between 100 and 700 volts.

28. The method of claim 20, wherein the non-defibrillatory electrical current pulses have an amplitude of between 100 and 1000 volts.

29. The method of claim 20, wherein the non-defibrillatory electrical current pulses have an amplitude of between 100 and 2000 volts.

30. The method of claim 20, wherein the non-defibrillatory electrical current pulses have an amplitude of between 0.02 and 25 joules.

31. The method of claim 20, wherein the non-defibrillatory electrical current pulses have an amplitude of between 0.25 and 10 amperes.

32. The method of claim 20, wherein the non-defibrillatory electrical current pulses have an amplitude of between 0.5 and 10 amperes.

33. The method of claim 20, wherein the non-defibrillatory electrical current pulses are composed of shorter pulses shorter than the at least one defibrillation pulse.

34. The system of claim 33, wherein the shorter pulses have pulse widths of between 20 us and about 2 ms.

35. The method of claim 20, wherein the non-defibrillatory electrical current pulses are composed of at least 10 shorter pulses shorter than the at least one defibrillation pulse.

36. The method of claim 20, wherein the non-defibrillatory electrical current pulses are composed of at most 50 shorter pulses shorter than the at least one defibrillation pulse.

37. The method of claim 20, wherein the step of delivering non-defibrillatory electrical current pulses is administered for a period of less than about 20 seconds.

38. The method of claim 20, wherein the at least one defibrillation pulse has an amplitude of between 25 and 360 joules.

39. A system, for external use on a human body, for maintaining some cardiac output of a patient's heart during arrhythmia using electrical current, comprising:
   a. a power supply;
   b. an arrhythmia detector connected to the power supply;
   c. capacitor charging circuitry connected to the power supply;
   d. output circuitry connected to the capacitor charging circuitry and the power supply for delivering at least one non-defibrillatory electrical current pulse through portions of the patient's upper body after detection of arrhythmia, the non-defibrillatory electrical current pulse having an amplitude less than the amplitude necessary to defibrillate the patient, and greater than that which would only pace the heart;
   e. output control circuitry connected to the arrhythmia detector, the power supply, the capacitor charging circuitry, and the first output circuitry, the output control circuitry providing pulses suitable for producing contraction in the patient's muscles sufficient to maintain a level of cardiac output which is a fraction of the normal maximum cardiac output; and
   f. the capacitor charging circuitry cooperating with the output control circuitry and the power supply and adapted for delivering at least one defibrillation pulse to the patient's body.

40. The system of claim 39, wherein the non-defibrillatory electrical current pulses have an amplitude of between 200 and 5000 watts.

41. The system of claim 39, wherein the non-defibrillatory electrical current pulses have an amplitude of between 12.5 and 5000 average watts.

42. The system of claim 39, wherein the non-defibrillatory electrical current pulses have an amplitude of between 100 and 400 volts.

43. The system of claim 39, wherein the non-defibrillatory electrical current pulses have an amplitude of between 100 and 500 volts.

44. The system of claim 39, wherein the non-defibrillatory electrical current pulses have an amplitude of between 100 and 700 volts.

45. The system of claim 39, wherein the non-defibrillatory electrical current pulses have an amplitude of between 100 and 1000 volts.

46. The system of claim 39, wherein the non-defibrillatory electrical current pulses have an amplitude of between 100 and 2000 volts.

47. The system of claim 39, wherein the non-defibrillatory electrical current pulses have an amplitude of between 0.02 and 25 joules.

48. The system of claim 39, wherein the non-defibrillatory electrical current pulses have an amplitude of between 0.25 and 10 amperes.

49. The system of claim 39, wherein the non-defibrillatory electrical current pulses have an amplitude of between 0.5 and 10 amperes.

50. The system of claim 39, wherein the non-defibrillatory electrical current pulses are composed of shorter pulses shorter than the at least one defibrillation pulse.

51. The system of claim 50, wherein the shorter pulses have pulse widths of between 20 us and 2 ms.

52. The system of claim 39, wherein the non-defibrillatory electrical current pulses are composed of at least 10 shorter pulses shorter than the at least one defibrillation pulse.

53. The system of claim 39, wherein the non-defibrillatory electrical current pulses are composed of at most 50 shorter pulses shorter than the at least one defibrillation pulse.

54. The system of claim 39, wherein the at least one defibrillation pulse have an amplitude of between 25 and 360 joules.

55. A system, for external use on a human body, for maintaining some cardiac output of a patient's heart during tachyarrhythmia using electrical current, comprising:
   a. a power supply;
   b. a tachyarrhythmia detector connected to the power supply;
   c. capacitor charging circuitry connected to the power supply;
   d. output circuitry connected to the capacitor charging circuitry and the power supply for delivering at least one non-defibrillatory electrical current pulse through portions of the patient's upper body, the non-defibrillatory electrical current pulses having an amplitude less than the amplitude necessary to defibrillate the patient, and greater than that which would only pace the heart;
   e. output control circuitry connected to the tachyarrhythmia detector, the power supply, the capacitor charging circuitry, and the output circuitry, the output control circuitry providing pulses suitable for producing contraction in the patient's muscles sufficient to maintain a level of cardiac output which is a fraction of the normal maximum cardiac output; and
   f. the capacitor charging circuitry cooperating with the output control circuitry and the power supply and adapted for delivering at least one defibrillation pulse to the patient's body.

56. The system of claim 55, wherein the non-defibrillatory electrical current pulses have an amplitude of between 200 and 5000 watts.

57. The system of claim 55, wherein the non-defibrillatory electrical current pulses have an amplitude of between 12.5 and 5000 average watts.

58. The system of claim 55, wherein the non-defibrillatory electrical current pulses have an amplitude of between 100 and 400 volts.

59. The system of claim 55, wherein the non-defibrillatory electrical current pulses have an amplitude of between 100 and 500 volts.

60. The system of claim 55, wherein the non-defibrillatory electrical current pulses have an amplitude of between 100 and 700 volts.

61. The system of claim 55, wherein the non-defibrillatory electrical current pulses have an amplitude of between 100 and 1000 volts.

62. The system of claim 55, wherein the non-defibrillatory electrical current pulses have an amplitude of between 100 and 2000 volts.

63. The system of claim 55, wherein the non-defibrillatory electrical current pulses have an amplitude of between 0.02 and 25 joules.

64. The system of claim 55, wherein the non-defibrillatory electrical current pulses have an amplitude of between 0.25 and 10 amperes.

65. The system of claim 55, wherein the non-defibrillatory electrical current pulses have an amplitude of between 0.5 and 10 amperes.

66. The system of claim 55, wherein the non-defibrillatory electrical current pulses are composed of shorter pulses shorter than the at least one defibrillation pulse.

67. The system of claim 66, wherein the shorter pulses have pulse widths of between 20 us and about 2 ms.

68. The system of claim 55, wherein the non-defibrillatory electrical current pulses are composed of at least 10 shorter pulses shorter than the at least one defibrillation pulse.

69. The system of claim 55, wherein the non-defibrillatory electrical current pulses are composed of at most 50 shorter pulses shorter than the at least one defibrillation pulse.

70. The system of claim 55, wherein the at least one defibrillation pulse has an amplitude of between 25 and 360 joules.

71. A tachyarrhythmia treating system, comprising:
   power supply means;
   arrhythmia detection means operably coupleable to the power supply means;
   pulse delivery means operably coupleable to the power supply means;
   output control means operably coupleable to the arrhythmia detection means, power supply means, and pulse delivery means;
   external defibrillation means operably coupleable with said output control means; and
   instructions recorded on a tangible medium for operating the system so as to treat an arrhythmia in a patient, the instructing including instructions to:
      attach the pulse delivery means to external portions of the patient's body proximate the patient's thoracic region so that the pulse delivery means can deliver electrical pulses which will be transmitted through portions of the patient's upper body;
      detect the presence of arrhythmia in the patient with the arrhythmia detection means;
      deliver non-defibrillatory electrical current pulses through the patient's body via the pulse delivery means after detecting an arrhythmia, the non-defibrillatory electrical current pulses having an amplitude of less than the amplitude of a normal defibrillation shock and greater than that which would only pace the heart, to force contraction of patient muscle and facilitate a minimum level of cardiac output; and deliver at least one defibrillation pulse having an amplitude sufficient to defibrillate the patient's heart with the external defibrillation means.

72. A tachyarrhythmia treating system, comprising:

a power supply;

an arrhythmia detector connected to the power supply;

capacitor charging circuitry connected to the power supply;

output circuitry connected to the capacitor charging circuitry and the power supply;

output control circuitry connected to the arrhythmia detector, the power supply, the capacitor charging circuitry, and the output circuitry, the output control circuitry providing pulses suitable for producing contraction in the patient's muscles sufficient to maintain a level of cardiac output which is a fraction of the normal maximum cardiac output;

the capacitor charging circuitry cooperating with the output control circuitry and the power supply and adapted for delivering at least one defibrillation pulse to the patient's body; and instructions recorded on a tangible medium for operating the system so as to treat an arrhythmia in a patient, the instructing including instructions to:

attach electrodes to external portions of the patient's body proximate the patient's thoracic region so that the output circuitry can deliver electrical pulses which will be transmitted through portions of the patient's upper body;

detect the presence of arrhythmia in the patient with the arrhythmia detector;

deliver non-defibrillatory electrical current pulses through the patient's body via the output circuitry after detecting an arrhythmia, the non-defibrillatory electrical current pulses having an amplitude of less than the amplitude of a normal defibrillation shock and greater than that which would only pace the heart, to force contraction of patient muscle and facilitate a minimum level of cardiac output; and deliver at least one defibrillation pulse having an amplitude sufficient to defibrillate the patient's heart.

* * * * *